(12) United States Patent
Przybyszewski et al.

(10) Patent No.: US 9,272,144 B2
(45) Date of Patent: Mar. 1, 2016

(54) LEAD ELECTRODE FOR USE IN AN MRI-SAFE IMPLANTABLE MEDICAL DEVICE

(71) Applicant: Medtronic, Inc., Minneapolis, MN (US)

(72) Inventors: Piotr Przybyszewski, Coon Rapids, MN (US); Carl D. Wahlstrand, Lino Lakes, MN (US); Timothy J. Davis, Coon Rapids, MN (US); Gregory A. Hrdlicka, Plymouth, MN (US); James M. Olsen, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 14/661,548

(22) Filed: Mar. 18, 2015

(65) Prior Publication Data

US 2015/0190640 A1 Jul. 9, 2015

Related U.S. Application Data

(63) Continuation of application No. 11/071,136, filed on Mar. 2, 2005, now Pat. No. 8,989,840.

(60) Provisional application No. 60/557,991, filed on Mar. 30, 2004.

(51) Int. Cl.
*A61B 5/05* (2006.01)
*A61N 1/36* (2006.01)
*A61N 1/37* (2006.01)
*A61N 1/05* (2006.01)
*A61N 1/08* (2006.01)

(52) U.S. Cl.
CPC .......... *A61N 1/36142* (2013.01); *A61N 1/3605* (2013.01); *A61N 1/36125* (2013.01); *A61N 1/3718* (2013.01); *A61N 1/0534* (2013.01); *A61N 1/0551* (2013.01); *A61N 1/36071* (2013.01); *A61N 2001/086* (2013.01)

(58) Field of Classification Search
CPC .. A61N 1/3718; A61N 1/08; A61N 2001/086
See application file for complete search history.

(56) References Cited

U.S. PATENT DOCUMENTS

| | | | |
|---|---|---|---|
| 6,949,929 B2 * | 9/2005 | Gray et al. | 324/318 |
| 2002/0116029 A1 * | 8/2002 | Miller et al. | 607/9 |
| 2003/0083723 A1 * | 5/2003 | Wilkinson et al. | 607/122 |
| 2003/0144721 A1 * | 7/2003 | Villaseca et al. | 607/122 |
| 2006/0155270 A1 * | 7/2006 | Hancock et al. | 606/33 |

* cited by examiner

*Primary Examiner* — Tammie K Heller
(74) *Attorney, Agent, or Firm* — Withers & Keys, LLC

(57) ABSTRACT

An implantable stimulation system comprises a stimulator for generating electrical stimulation and a conductive stimulation lead having a proximal end electrically coupled to the stimulator, wherein at least a first component of the impedance looking into the stimulator is substantially matched to the impedance of the stimulation lead. At least one distal stimulation electrode is positioned proximate the distal end of the stimulation lead.

7 Claims, 9 Drawing Sheets

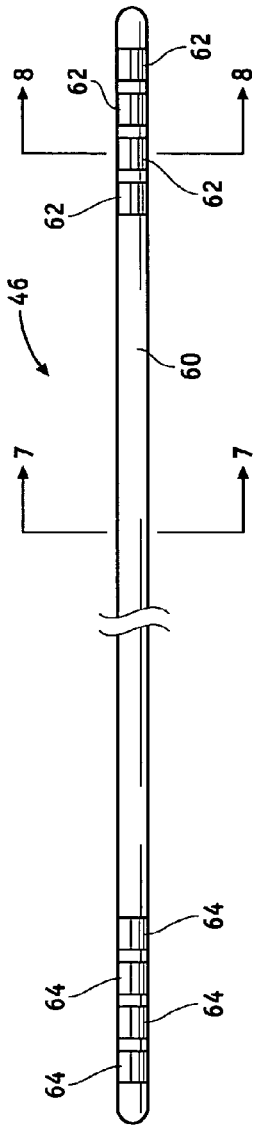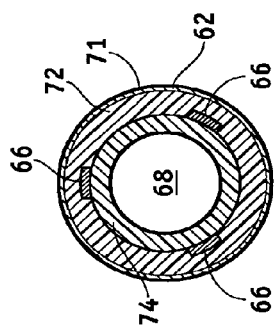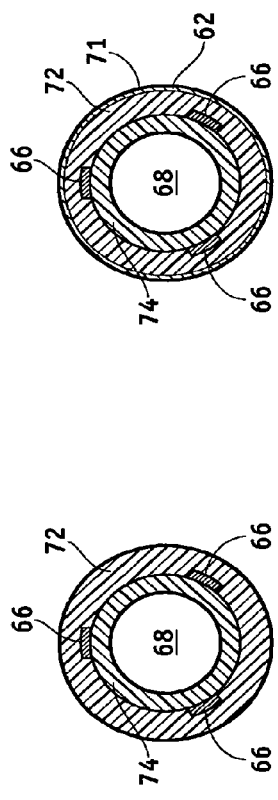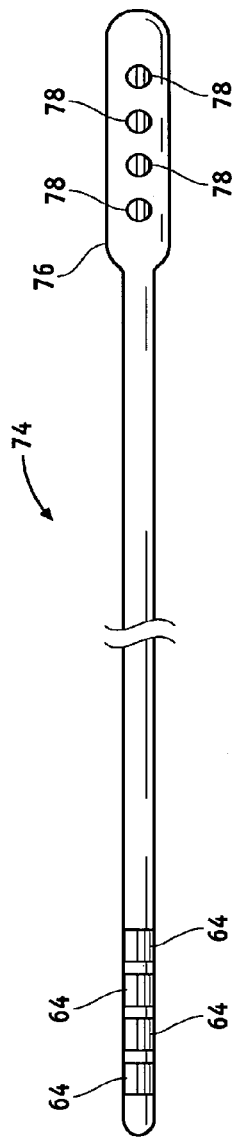

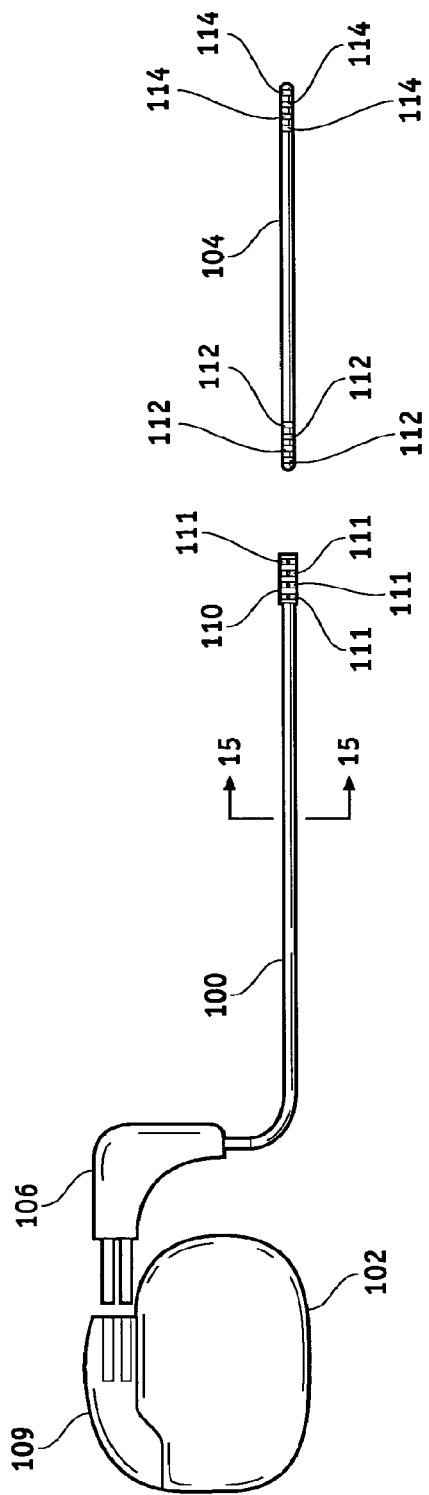
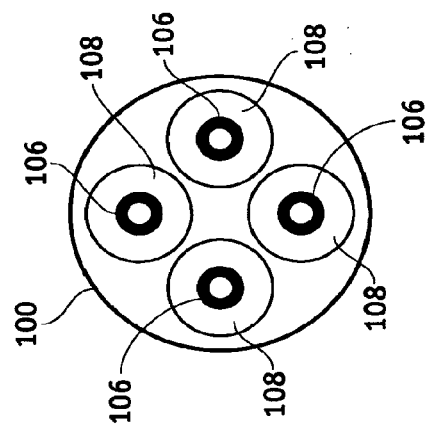
FIG. 14
FIG. 15

LEAD ELECTRODE FOR USE IN AN MRI-SAFE IMPLANTABLE MEDICAL DEVICE

CROSS-REFERENCES TO RELATED APPLICATIONS

This application claims the benefit of U.S. Provisional Application No. 60/557,991, filed Mar. 30, 2004.

FIELD OF THE INVENTION

The present invention generally relates to implantable medical devices, and more particularly to an implantable MRI-safe stimulation lead for use in conjunction with an implantable medical device wherein the impedance of the implanted medical device is matched to that of the stimulation lead for decreasing the generation of heat at the lead's stimulation electrodes.

BACKGROUND OF THE INVENTION

Implantable medical devices are commonly used today to treat patients suffering from various ailments. Such implantable devices may be utilized to treat conditions such as pain, incontinence, sleep disorders, and movement disorders such as Parkinson's disease and epilepsy. Such therapies also appear promising in the treatment of a variety of psychological, emotional, and other physiological conditions.

One known type of implantable medical device, a neurostimulator, delivers mild electrical impulses to neural tissue using an electrical lead. For example, to treat pain, electrical impulses may be directed to specific sites. Such neurostimulation may result in effective pain relief and a reduction in the use of pain medications and/or repeat surgeries.

Typically, such devices are totally implantable and may be controlled by a physician or a patient through the use of an external programmer. Current systems generally include a non-rechargeable primary cell neurostimulator, a lead extension, and a stimulation lead, and the two main classes of systems may be referred to as: (1) Spinal Cord Stimulation (SCS) and (2) Deep Brain Stimulation (DBS).

An SCS stimulator may be implanted in the abdomen, upper buttock, or pectoral region of a patient and may include at least one extension running from the neurostimulator to the lead or leads which are placed somewhere along the spinal cord. Each of the leads (to be discussed in detail hereinbelow) currently contains from one to eight electrodes. Each extension (likewise to be discussed in detail below) is plugged into or connected to the neurostimulator at a proximal end thereof and is coupled to and interfaces with the lead or leads at a distal end of the extension.

The implanted neurostimulation system is configured to send mild electrical pulses to the spinal cord. These electrical pulses are delivered through the lead or leads to regions near the spinal cord or a nerve selected for stimulation. Each lead includes a small insulated wire coupled to an electrode at the distal end thereof through which the electrical stimulation is delivered. Typically, the lead also comprises a corresponding number of internal wires to provide separate electrical connection to each electrode such that each electrode may be selectively used to provide stimulation. Connection of the lead to an extension may be accomplished by means of a connector block including, for example, a series or combination of set screws, ball seals, etc. The leads are inserted into metal set screw hocks, and the metal set screws are manipulated to press the contacts against the blocks to clamp them in place and provide electrical connection between the lead wires and the blocks. Such an arrangement is shown in U.S. Pat. No. 5,458,629 issued Oct. 17, 1995 and entitled "Implantable Lead Ring Electrode and Method of Making".

A DBS system comprises similar components (i.e. a neurostimulator, at least one extension, and at least one stimulation lead) and may be utilized to provide a variety of different types of electrical stimulation to reduce the occurrence or effects of Parkinson's disease, epileptic seizures, or other undesirable neurological events. In this case, the neurostimulator may be implanted into the pectoral region of the patient. The extension or extensions may extend up through the patient's neck, and the leads/electrodes are implanted in the brain. The leads may interface with the extension just above the ear on both sides of the patient. The distal end of the lead may contain from four to eight electrodes and, as was the case previously, the proximal end of the lead may be connected to the distal end of the extension and may be held in place by set screws. The proximal portion of the extension plugs into the connector block of the neurostimulator.

Magnetic resonance imaging (MRI) is a relatively new and efficient technique that may be used in the diagnosis of many neurological disorders. It is an anatomical imaging tool which utilizes non-ionizing radiation (i.e. no x-rays or gamma rays) and provides a non-invasive method for the examination of internal structure and function. For example, MRI permits the study of the overall function of the heart in three dimensions significantly better than any other imaging method. Furthermore, imaging with tagging permits the non-invasive study of regional ventricular function.

MRI scanning is widely used in the diagnosis of injuries to the head. In fact, the MRI is now considered by many to be the preferred standard of care, and failure to prescribe MRI scanning can be considered questionable. Approximately sixteen million MRIs were performed in 1996, followed by approximately twenty million in the year 2000. It is projected that forty million MRIs will be performed in 2004.

In an MRI scanner, a magnet creates a strong magnetic field which aligns the protons of hydrogen atoms in the body and then exposes them to radio frequency (RF) energy from a transmitter portion of the scanner. This spins the various protons, and they produce a faint signal that is detected by a receiver portion of the scanner. A computer renders these signals into an image. During this process, three electromagnetic fields are produced; i.e. (1) a static magnetic field, (2) a gradient magnetic field, and (3) a radio frequency (RF) field. The main or static magnetic field may typically vary between 0.2 and 3.0 Tesla. A nominal value of 1.5 Tesla is approximately equal to 15,000 Gauss which is 30,000 times greater than the Earth's magnetic field of approximately 0.5 Gauss. The time varying or gradient magnetic field may have a maximum strength of approximately 40 milli-Tesla/meters at a frequency of 0-5 KHz. The RF may, for example, produce thousands of watts at frequencies of between 8-215 MHz. For example, up to 20,000 watts may be produced at 64 MHz and a static magnetic field of 1.5 Tesla; that is, 20 times more power than a typical toaster. Thus, questions have arisen regarding the potential risk associated with undesirable interaction between the MRI environment and the above-described neurostimulation systems; e.g. forces and torque on the implantable device within the MRI scanner caused by the static magnetic field, RF-induced heating, induced currents due to gradient magnetic fields, device damage, and image distortion. Of these interactions, the problems associated with induced RF currents in the leads are most deserving of attention since it has been found that the temperature in the leads can rise by as much as 25° Centigrade or higher in an MRI environment.

A similar problem occurs when a patient undergoes diathermy treatment employing RF energy to create eddy currents in the patient's tissue so as to heat the tissue and promote healing. In this environment, current may also be produced in the implanted lead causing undesirable heating of the electrodes as described above.

Accordingly, it would be desirable to provide an implantable medical device that may be safely operated in an MRI environment. It would be further desirable to provide an implantable medical device such as a SCS or DBS neurostimulation system that may be operated in an MRI environment without the generation of significant heat in the leads due to induced RF currents. It would be further desirable to provide an MRI-safe, implantable medical device wherein the generation of heat at the stimulation electrodes is reduced by matching the impedance of the device to that of its stimulation lead. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

According to a broad aspect of the invention, there is provided an implantable stimulation system comprising a stimulator for generating electrical stimulations, a conductive stimulation lead having a proximal end electrically coupled to the stimulator, and at least one distal stimulation electrode positioned proximate the distal end of the stimulation lead. At least a first component of the impedance looking into said stimulator is substantially matched to the impedance of the stimulation lead,

BRIEF DESCRIPTION OF THE DRAWINGS

The present invention will hereinafter be described in conjunction with the following drawing figures, wherein like numerals denote like elements, and:

FIG. 6 is a top view of the lead shown in FIG. 2;

FIGS. 7 and 8 are cross-sectional views taken along lines 7-7 and 8-8, respectively, in FIG. 6;

FIG. 9 is a top view of an alternate lead configuration;

FIG. 14 is an exploded view of a neurostimulation system;

FIG. 15 is a cross-sectional view of the extension shown in FIG. 14 taken along line 15-15;

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
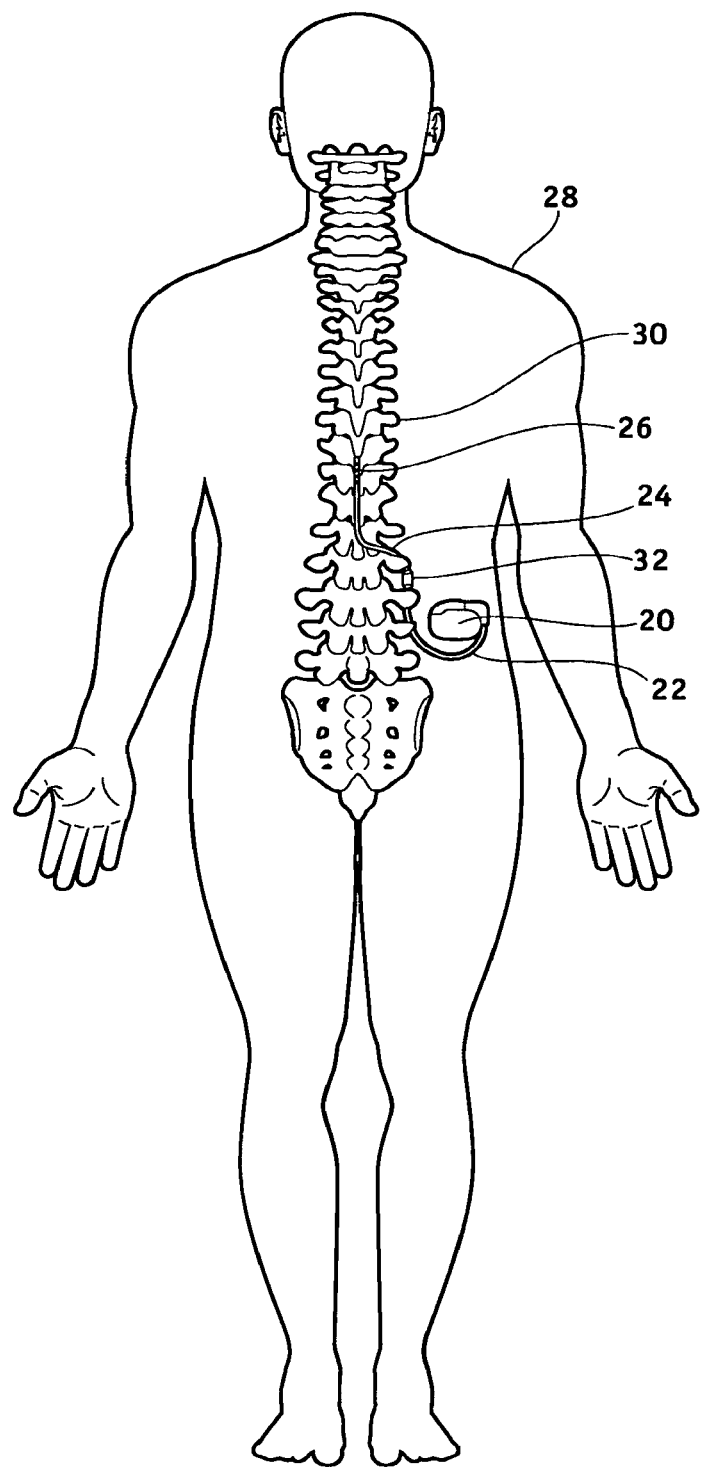
FIG. 1 illustrates a typical spinal cord stimulation system implanted in a patient.

FIG. 1 illustrates a typical SCS system implanted in a patient. As can be seen, the system comprises a pulse generator such as an SCS neurostimulator 20, a lead extension 22 having a proximal end coupled to neurostimulator 20 as will be more fully described below, and a lead 24 having proximal end coupled to the distal end of extension 22 and having a distal end coupled to one or more electrodes 26. Neurostimulator 20 is typically placed in the abdomen of a patient 28, and lead 24 is placed somewhere along spinal cord 30. As stated previously, neurostimulator 20 may have one or two leads each having four to eight electrodes. Such a system may also include a physician programmer and a patient programmer (not shown). Neurostimulator 20 may be considered to be an implantable pulse generator of the type available from Medtronic, Inc. and capable of generating multiple pulses occurring either simultaneously or one pulse shifting in time with respect to the other, and having independently varying amplitudes and pulse widths. Neurostimulator 20 contains a power source and the electronics for sending precise, electrical pulses to the spinal cord to provide the desired treatment therapy. While neurostimulator 20 typically provides electrical stimulation by way of pulses, other forms of stimulation may be used as continuous electrical stimulation.

Lead 24 is a small medical wire having special insulation thereon and includes one or more insulated electrical conductors each coupled at their proximal end to a connector and to contacts/electrodes 26 at its distal end. Some leads are designed to be inserted into a patient percutaneously (e.g. the Model 3487A Pisces—Quad® lead available from Medtronic, Inc.), and some are designed to be surgically implanted (e.g. Model 3998 Specify® lead, also available form Medtronic, Inc.). Lead 24 may contain a paddle at its distant end for housing electrodes 26; e.g. a Medtronic paddle having model number 3587A. Alternatively, electrodes 26 may comprise one or more ring contacts at the distal end of lead 24 as will be more fully described below.

While lead 24 is shown as being implanted in position to stimulate a specific site in spinal cord 30, it could also be positioned along the peripheral nerve or adjacent neural tissue ganglia or may be positioned to stimulate muscle tissue. Furthermore, electrodes 26 may be epidural, intrathecal or placed into spinal cord 30 itself. Effective spinal cord stimulation may be achieved by any of these lead placements.

While the lead connector at proximal end of lead 24 may be coupled directly to neurostimulator 20, the lead connector is typically coupled to lead extension 22 as is shown in FIG. 1. An example of a lead extension is Model 7495 available from Medtronic, Inc.

A physician's programmer (not shown) utilizes telemetry to communicate with the implanted neurostimulator 20 to enable the physician to program and manage a patient's therapy and troubleshoot the system. A typical physician's programmer is available from Medtronic, Inc. and bears Model No. 7432. Similarly, a patient's programmer (also not shown) also uses telemetry to communicate with neurostimulator 20 so as to enable the patient to manage some aspects of their own therapy as defined by the physician. An example of a patient programmer is Model 7434® 3 EZ Patient Programmer available from Medtronic, Inc.

Implantation of a neurostimulator typically begins with the implantation of at least one stimulation lead usually while the patient is under a local anesthetic. While there are many spinal cord lead designs utilized with a number of different implantation techniques, the largest distinction between leads revolves around how they are implanted. For example, surgical leads have been shown to be highly effective, but require a laminectomy for implantation. Percutaneous leads can be introduced through a needle, a much easier procedure. To simplify the following explanation, discussion will focus on percutaneous lead designs, although it will be understood by those skilled in the art that the inventive aspects are equally applicable to surgical leads. After the lead is implanted and positioned, the lead's distal end is typically anchored to minimize movement of the lead after implantation. The lead's proximal end is typically configured to connect to a lead extension 22. The proximal end of the lead extension is then connected to the neurostimulator 20.

Figure 2:
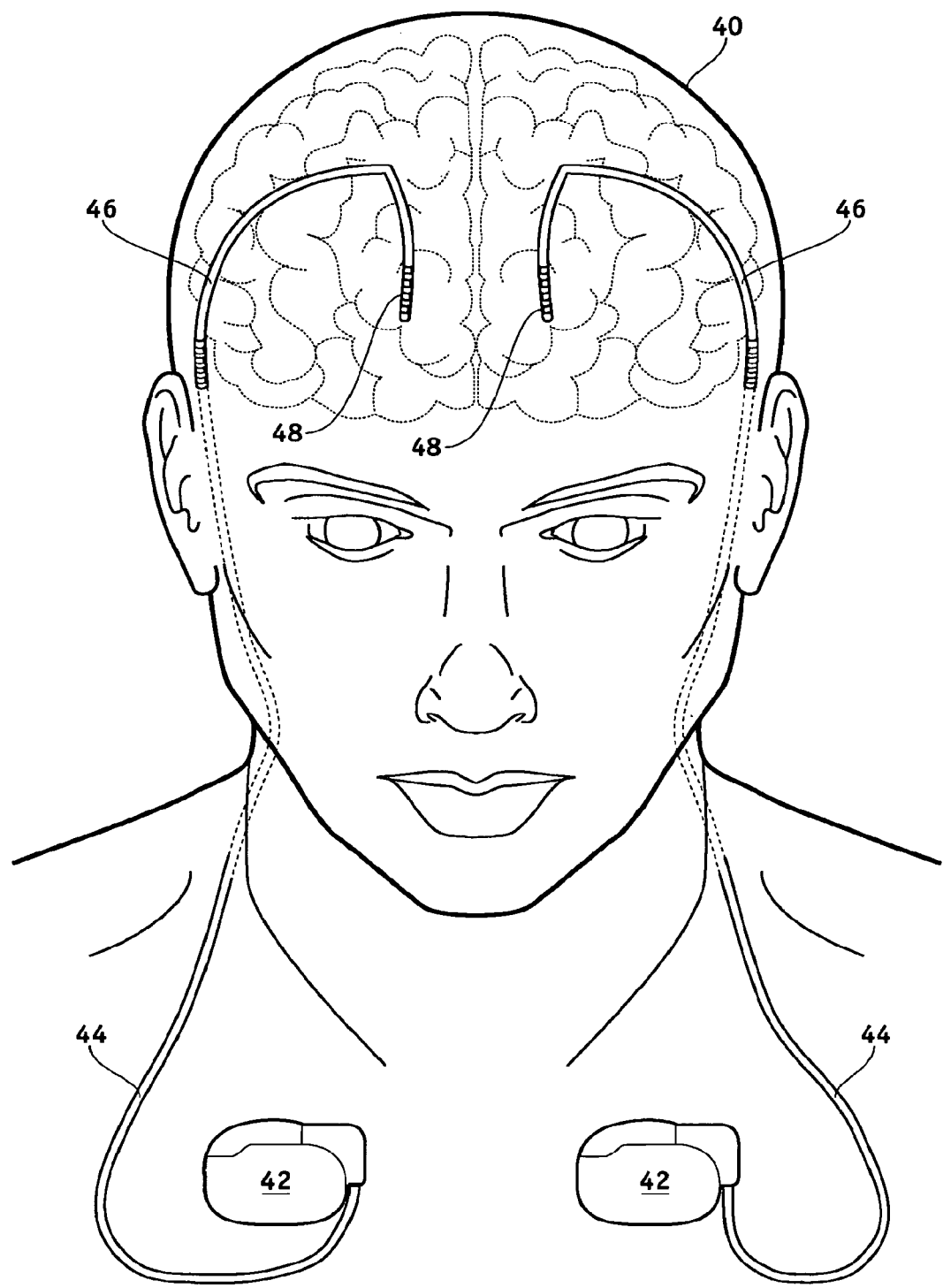
FIG. 2 illustrates a typical deep brain stimulation system implanted in a patient.

FIG. 2 illustrates a DBS system implanted in a patient 40 and comprises substantially the same components as does an SCS; that is, at least one neurostimulator, at least one extension, and at least one stimulation lead containing one or more electrodes. As can be seen, each neurostimulator 42 is implanted in the pectoral region of the patient. Extensions 44 are deployed up through the patient's neck, and leads 46 are implanted in the patient's brain is as shown at 48. As can be seen, each of the leads 46 is connected to its respective extension 44 just above the ear on both sides of patient 40.

Figure 5:
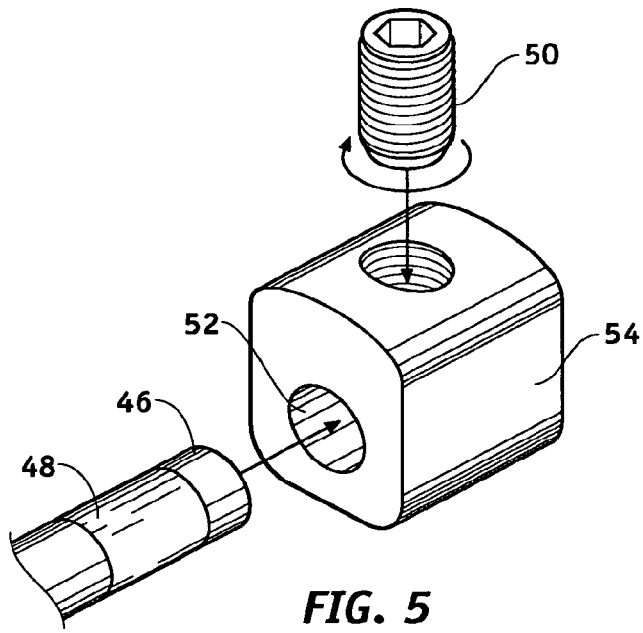
FIG. 5 is an isometric view of an example of a connector screw block suitable for connecting the lead of FIG. 3 to the extension shown in FIG. 4.
Figure 3:
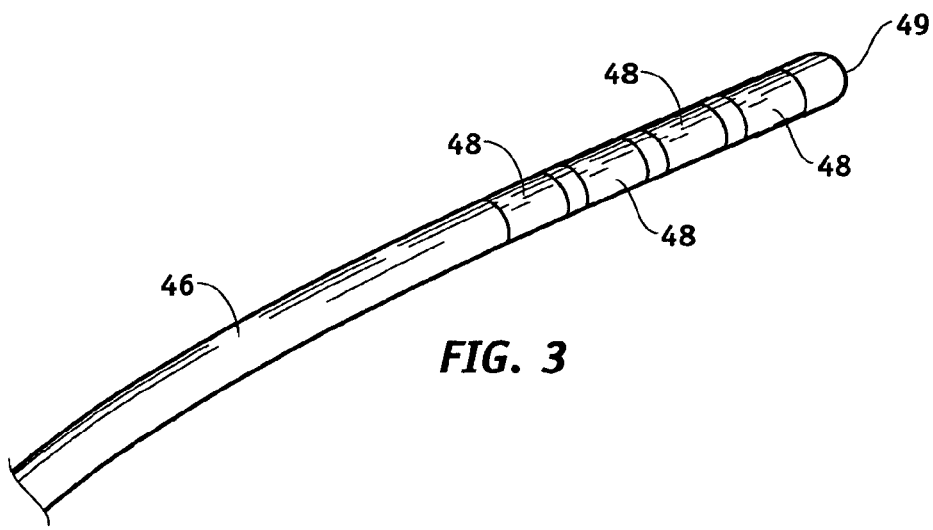
FIG. 3 is an isometric view of the distal end of the lead shown in FIG. 2.
Figure 4:
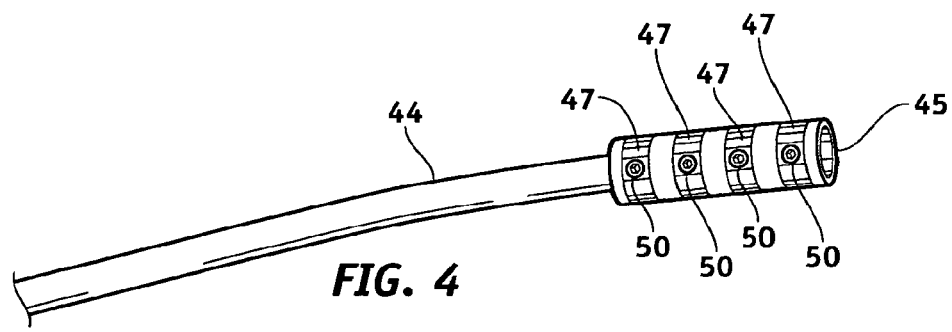
FIG. 4 is an isometric view of the distal end of the extension shown in FIG. 2.

FIG. 3 is an isometric view of the distal end of lead 46. In this case, four ring electrodes 48 are positioned on the distal end of lead 46 and coupled to internal conductors or filers (not shown) contained within lead 46. Again, while four ring electrodes are shown in FIG. 3, it is to be understood that the number of electrodes can vary to suit a particular application. FIG. 4 is an isometric view of the distal end of extension 44, which includes a connector portion 45 having four internal contacts 47. The proximal end of the DBS lead is shown in FIG. 3, plugs into the distal connector 45 of extension 44, and is held in place by means of, for example, a plurality (e.g. 4) of set screws 50. For example, referring to FIG. 5, lead 46 terminates in a series of proximal electrical ring contacts 48 (only one of which is shown in FIG. 5). Lead 46 may be inserted through an axially aligned series of openings 52 (again only one shown) in screw block 54. With a lead 46 so inserted, a series of set screws (only one shown) are screwed into block 54 to drive contacts 48 against blocks 54 and secure and electrically couple the lead 46. It should be appreciated, however, that other suitable methods for securing lead 46 to extension 44 may be employed. The proximal portion of extension 44 is secured to neurostimulator 42 as is shown in FIGS. 1 and 2.

FIG. 6 is a top view of lead 46 shown in FIG. 2. FIGS. 7 and 8 are cross-sectional views taken along lines 7-7 and 8-8, respectively, in FIG. 6. Distal end 60 of lead 46 includes at least one electrode 62 (four are shown). As stated previously, up to eight electrodes may be utilized. Each of electrodes 62 is preferably constructed as is shown in FIG. 8. That is, electrode 62 may comprise a conductive ring 71 on the outer surface of the elongate tubing making up distal shaft 60. Each electrode 62 is electrically coupled to a longitudinal wire 66 (shown in FIGS. 7 and 8) each of which extends to a contact 64 at the proximal end of lead 46: Longitudinal wires 66 may be of a variety of configurations; e.g. discreet wires, printed circuit conductors, etc. From the arrangement shown in FIG. 6, it should be clear that four conductors or filers run through the body of lead 46 to electrically connect the proximal electrodes 64 to the distal electrodes 62. As will be further discussed below, the longitudinal conductors 66 may be spirally configured along the axis of lead 46 until they reach the connector contacts.

The shaft of lead 46 preferably has a lumen 68 extending therethrough for receiving a stylet that adds a measure of rigidity during installation of the lead. The shaft preferably comprises a comparatively stiffer inner tubing member 70 (e.g. a polyamine, polyamide, high density polyethylene, polypropylene, polycarbonate or the like). Polyamide polymers are preferred. The shaft preferably includes a comparatively softer outer tubing member 72; e.g. silicon or other suitable elastomeric polymer. Conductive rings 71 are preferably of a biocompatible metal such as one selected from the noble group of metals, preferably palladium, platinum or gold and their alloys.

FIG. 9 illustrates an alternative lead 74 wherein distal end 76 is broader (e.g. paddle-shaped) to support a plurality of distal electrodes 78. A lead of this type is shown in FIG. 1. As was the case with the lead shown in FIGS. 6,7, and 8, distal electrodes 78 are coupled to contacts 64 each respectively by means of an internal conductor or filer. A more detailed description of the leads shown in FIGS. 6 and 9 may be found in U.S. Pat. No. 6,529,774 issued Mar. 4, 2003 and entitled "Extradural Leads, Neurostimulator Assemblies, and Processes of Using Them for Somatosensory and Brain Stimulation".

Figure 11:
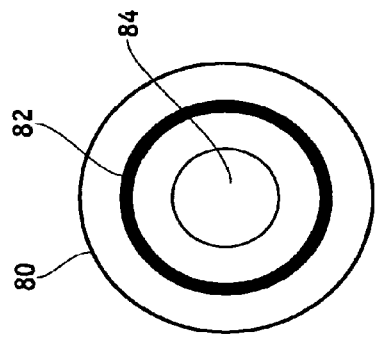
FIGS. 10 and 11 are longitudinal and radial cross-sectional views of a helically wound lead of the type shown in FIG. 6.
Figure 10:
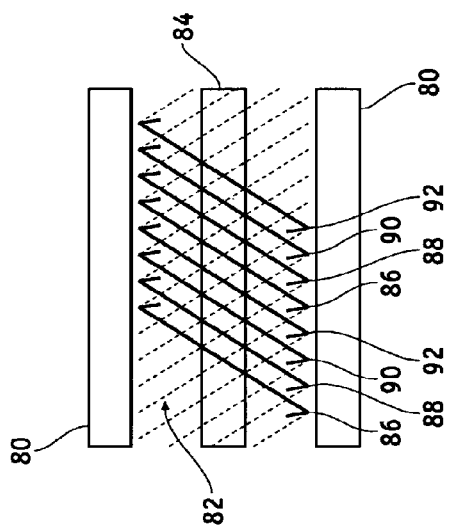

Leads of the type described above may be of the wound helix filer type or of the cabled filer type. FIGS. 10 and 11 are longitudinal and radial cross-sectional views, respectively, of a helically wound lead of the type shown in FIG. 6. The lead comprises an outer lead body 80; a plurality of helically wound, co-radial lead filers 82; and a stylet lumen 84. As stated previously, a stylet is a stiff, formable insert placed in the lead during implant so as to enable the physician to steer the lead to an appropriate location. FIG. 10 illustrates four separate, co-radially wound filers 86, 88, 90, and 92 which are electrically insulated from each other and electrically couple a single electrode 62 (FIG. 6) to a single contact 64 (FIG. 6).

Figure 13:
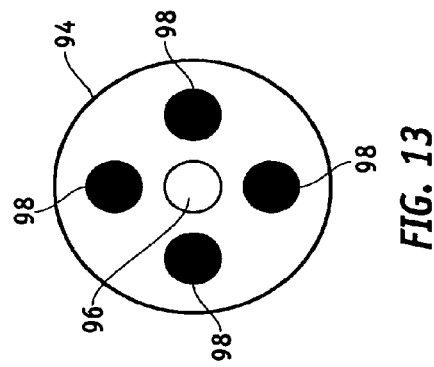
FIGS. 12 and 13 are longitudinal and radial cross-sectional views, respectively, of a cabled lead.
Figure 12:
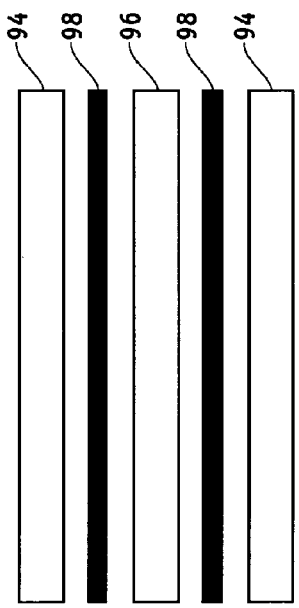

As can be seen, lead filers 82 have a specific pitch and form a helix of a specific diameter. The helix diameter is relevant in determining the inductance of the lead. These filers themselves also have a specific diameter and are made of a specific material. The filer diameter, material, pitch and helix diameter are relevant in determining the impedance of the lead. In the case of a helically wound lead, the inductance contributes to a frequency dependent impedance. FIGS. 12 and 13 are longitudinal and radially cross-sectional views, respectively, of a cabled lead. The lead comprises outer lead body 94, stylet lumen 96, and a plurality (e.g. four to eight) of straight lead filers 98.

FIG. 14 is an exploded view of a neurostimulation system that includes an extension 100 configured to be coupled between a neurostimulator 102 and lead 104. The proximal portion of extension 100 comprises a connector 106 configured to be received or plugged into connector block 109 of neurostimulator 102. The distal end of extension 100 likewise comprises a connector 110 including internal contacts 111 and is configured to receive the proximal end of lead 104 having contacts 112 thereon. The distal end of lead 104 includes distal electrodes 114.

FIG. 15 is a cross-sectional view of extension 100. Lead extension 100 has a typical diameter of 0.1 inch, which is significantly larger than that of lead 104 so as to make extension 100 more durable than lead 104. Extension 100 differs from lead 104 also in that each filer 106 in lead body is helically wound or coiled in its own lumen 108 and not co-radially wound with the rest of the filers as was the case in lead 104.

The diameter of typical percutaneous leads is approximately 0.05 inch. This diameter is based upon the diameter of the needle utilized in the surgical procedure to deploy the lead and upon other clinical anatomical requirements. The length of such percutaneous SCS leads is based upon other clinical anatomical requirements. The length of such percutaneous SCS leads is typically 28 centimeters; however, other lengths are utilized to meet particular needs of specific patients and to accommodate special implant locations.

Lead length is an important factor in determining the suitability of using the lead in an MRI environment. For example, the greater length of the lead, the larger the effective loop area that is impacted by the electromagnetic field (e.g. the longer the lead, the larger the antenna). Furthermore, depending on the lead length, there can be standing wave effects that create areas of high current along the lead body. This can be problematic if the areas of high current are near the distal electrodes.

Compared to the helically wound lead, the cable lead has smaller DC resistance because the length of the straight filer is less than that of a coiled filer and the impedance at frequency is reduced because the inductance has been significantly reduced. It has been determined that the newer cabled filer designs tend to be more problematic in an MRI environment than do the wound helix filer designs. It should be noted that straight filers for cable leads sometimes comprise braided stranded wire that includes a number of smaller strands woven to make up each filer. This being the case, the number of strands could be varied to alter the impedance.

In copending U.S. patent application Ser. No. 10/945,739 assigned to the assignee of the present invention, it was shown that high lead impedances at MRI operational frequencies can reduce the heating of an electrode during an MRI procedure. The high impedance acts as a choke for current flowing through the lead and increases real losses along the length of the lead. These two mechanisms reduce electrode heating. As previously alluded to, leads have been intentionally designed with low impedance to enhance system stimulation efficiency. The simplest way to increase the impedance of a lead is to increase its DC resistance. This may be accomplished in a number of ways that may, if desired, be combined to achieve optimal impedance. For example, the resistance R of a lead filer is governed by the equation:

$$R = \frac{L}{\sigma a} \quad \text{Equation (1)}$$

where R is the resistance, L is the length of the filer, σ is the conductivity, and α is the cross-sectional area. Decreasing the conductivity and/or the cross-sectional area of the filer will increase resistance proportionally.

Impedance can also be obtained through inductance in accordance with the equation:

$$Z = j(2\pi f)L \quad \text{Equation (2)}$$

where Z is the impedance, L is the inductance, and f is the frequency. Inductance L may be either distributed or discrete. For example, distributed inductance can be created by helically coiling the lead filers in such a way as to achieve the above described optimal impedance at MR frequencies. The inductance is governed by the equation:

$$L = \frac{\mu N^2 A}{l} \quad \text{Equation (3)}$$

where N is the number of turns in the helix, A is the cross-sectional area, l is the length, and μ is the permeability.

It has also been discovered that electrode heating during an MRI procedure can be reduced if the impedance looking into the implantable pulse generator (IPG) and the characteristic impedance of the lead are substantially matched. For purposes of this discussion the term "lead" is considered to represent the stimulation path (i.e. the path that therapy pulses generated by the IPG propagate to reach a stimulation electrode) between the IPG and the stimulation electrodes. That is, for example, in the case of the arrangement shown in FIG. 14, the lead comprises a stimulation path through connector 106, extension 100, contact 111, contact 112, lead 104, and electrode 114.

As is well known, impedance may be represented by:

$$Z = A + jB \quad \text{Equation (4)}$$

where A represents a real component and jB represents an imaginary component. Thus, a first level of impedance matching is real impedance matching; i.e. the real impedance component of the IPG and the real impedance component of the lead are substantially matched;

$$A_{IPG} = A_{LEAD} \quad \text{Equation (5)}$$

Figure 16:
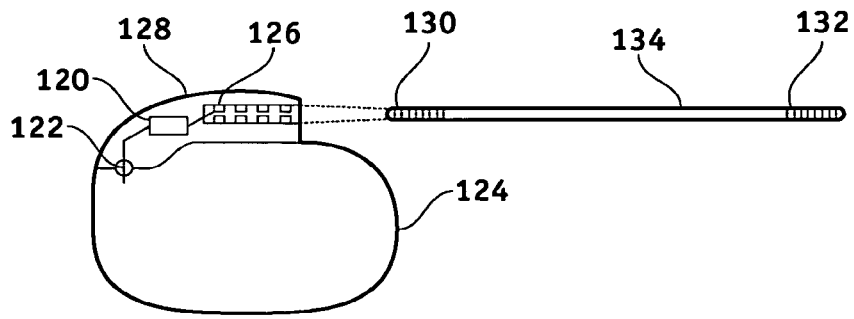
FIG. 16 illustrates a first embodiment of the present invention employing a matching impedance in the stimulation path.
Figure 17:
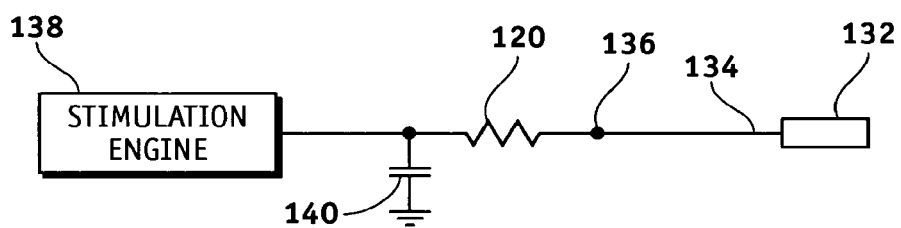
FIG. 17 is a schematic diagram of the embodiment shown in FIG. 16.

Referring to FIG. 16, a matching resistor 120 may be placed between feedthrough 122 of IPG housing 124 and a contact 126 in connector block 128 (e.g. made of silicone). As described above, a contact 130 electrically coupled to stimulation electrode 132 by means of a conductive filer (98 in FIG. 12) makes electrical contact with contact 126 when lead 134 is inserted into connector block 128. Thus, it can be seen from FIG. 17 that after determining the real impedance of lead 134 by measuring from point 136 into the lead, a matching resistor 120 may be placed between point 136 and stimulation engine 138 (i.e. that portion of the IPG circuitry that generates the therapy pulses) that results in a reduction in the heat generated at electrode 132 at high frequency. Capacitor 140 in FIG. 17 represents the feedthrough capacitance referred to above and dissipates any fluctuations occurring at high frequency to a reference potential; e.g. the stimulation engine encasement.

This solution is especially useful in the case of leads having a low DC resistance as may be illustrated by referring to Equation (6);

$$Z_o = \sqrt{\frac{R+j\omega L}{G+j\omega C}} \qquad \text{Equation (6)}$$

where $Z_o$ is the characteristic impedance, R is resistance, G is conductance, L is inductance, C is capacitance and $\omega=2\pi f$ where f is frequency. If R and G are low, they can be ignored, and the terms $j\omega$ in the numerator and denominator cancel leaving only the ratio of inductance (L) to capacitance (C) thus resulting in a real impedance (Z).

Figure 18:
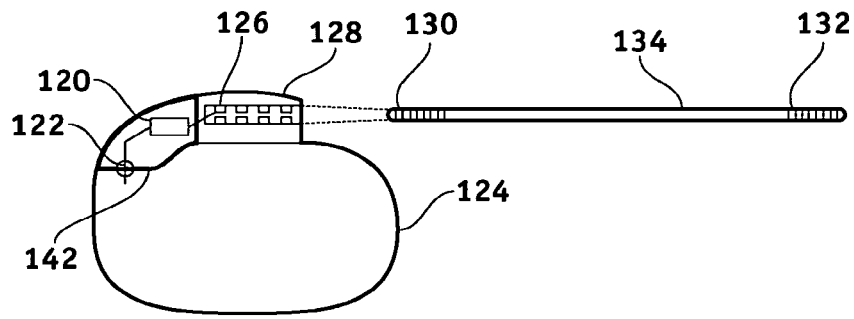
FIG. 18 is a side view of the embodiment shown in FIGS. 1 and 2 utilizing a separate hermetic encasement for the matching impedance.

Referring again to FIG. 16, resistor 120 may be a wound, thin film, or carbon-based resistor. Furthermore, resistor 120 may be attached to feedthrough pin 122 and contact 126 by crimping, spot welding, or through the use of a conductive adhesive. Finally, resistor 120 may be protected from exposure to the potential hostile environment inside a patient's body. A separate hermetic housing 142 may be provided for housing resistor 120 as is shown in FIG. 18. This will help prevent variations in impedance due to body fluid leakage and contact with resistor 120.

Figure 19:
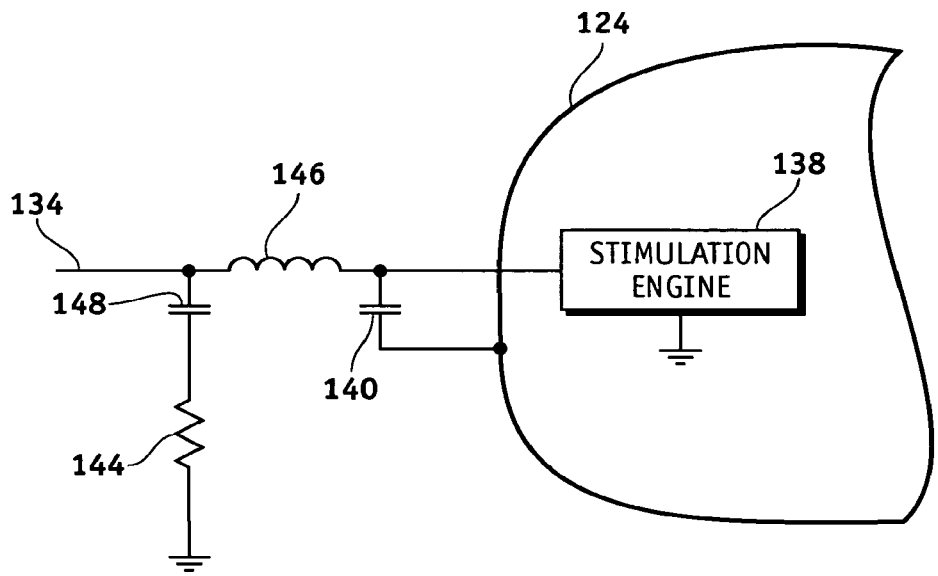
FIG. 19 is a schematic diagram of a second embodiment of the present invention employing a matching impedance outside the stimulation path.

If desired, a matching resistor 144 may be provided that is not in series with the stimulation path as is shown in FIG. 19. In this case an inductor 146 is coupled between stimulation engine 138 and the series combination of capacitor 148 and matching resistor 144. Inductor 146 acts as an open circuit at high frequency, and capacitor 148 acts as a short circuit at high frequency. Thus, high frequency current such as the current induced in lead 134 during an MRI procedure is dissipated through resistor 144. At the same time, stimulation efficiency is not significantly reduced because current does not flow through capacitor 148, (and therefore resistor 144), at stimulation frequencies. Capacitor 148 may be a mica or tantalum capacitor; however capacitor 148 is preferably ceramic so as to withstand exposure to body fluids without serious degradation over significant periods of time. Inductance 146 may be a wound conductor (e.g. a coil). As was the case previously, these components may be configured outside the hermetic IPG encasement 124 or inside a separate hermetic housing of the type shown in FIG. 18.

Figure 20:
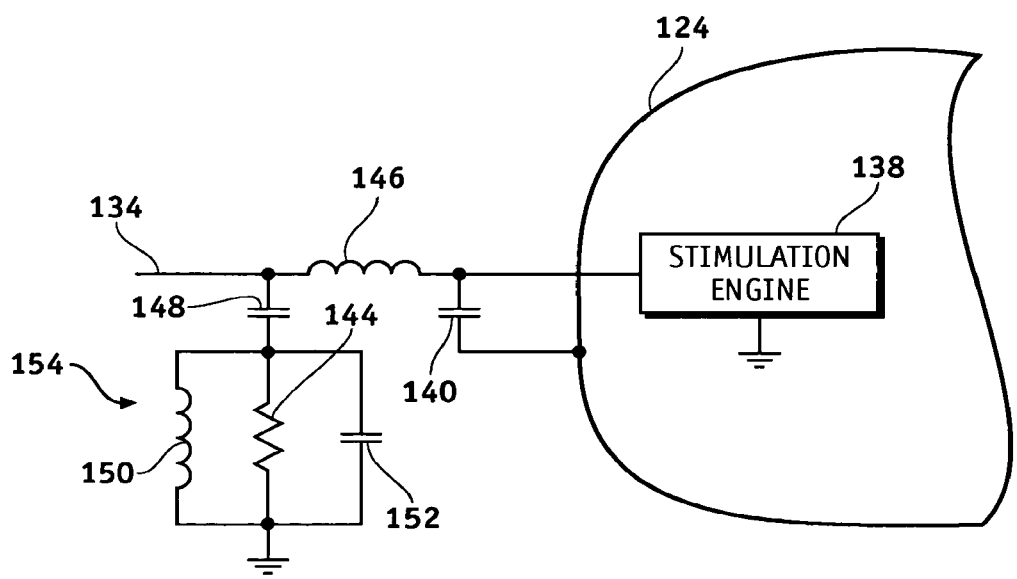
FIG. 20 is a schematic diagram of a third embodiment of the present invention for matching a complex impedance.

For complex impedance matching, the complex conjugate (Equation 4) of the characteristic impedance of lead 134 matches the complex impedance looking into stimulation engine 138 as is shown in FIG. 20. Obviously, the impedance of leads having significant resistance and/or conductance cannot be easily matched with real impedance. Therefore, an inductor 150 and/or capacitor 152 is included in matching circuit 154 and selected in accordance with known impedance matching techniques.

Since the characteristic impedance of lead 134 varies with frequency, lead routing, axial lead extension or compression, aging, exposure to body fluids, etc., it would be desirable to provide a mechanism for actively monitoring lead impedance and adjusting the matching impedance accordingly so as to provide a good match at different frequencies and under different conditions. This may be accomplished by means of an impedance monitoring and adjustment circuit 160 comprising a comparator 162, a microprocessor 164, and a switched impedance circuit 166. Comparator 162 has a first input coupled to node 168, a second input coupled to a first output of microprocessor 164, and an output coupled to an input of microprocessor 164. Microprocessor 164 has a second output coupled to an input of switched impedance circuit 166 which, in turn has an output coupled to node 168. Switched impedance circuit 166 is shown, for simplicity, as comprising a plurality of capacitors 170 coupled in parallel, each one coupled in series with one of a plurality of switches 172; however, it should be clear that switched impedance circuit 166 may contain a plurality of capacitors, inductors, resistors, switches, and related circuitry so as to selectively provide a wide range of impedance under the control of microprocessor 164.

The active impedance adjusting circuit shown in FIG. 21 operates as follows. The first input of comparator 162 is coupled to a potential corresponding to the voltage drop across resistor 144. The second input of comparator 162 is initially coupled to a predetermined voltage established by microprocessor 164. Under the control of microprocessor 164, capacitors 170 are switched into and out of the circuit so as to achieve the maximum voltage drop across resistor 144 indicative of an impedance that is substantially matched to that of lead 134. The predetermined voltage generated by microprocessor 164 and applied to the second input of comparator 162 is periodically updated to reflect the previous maximum voltage drop across resistor 144. By continually comparing the voltage at node 168 to the last maximum value of that voltage, impedance switching circuit 166 is adjusted to substantially maintain the voltage at node 168 at a maximum value and thereby maintain an impedance that substantially matches the impedance looking into the lead.

Figure 21:
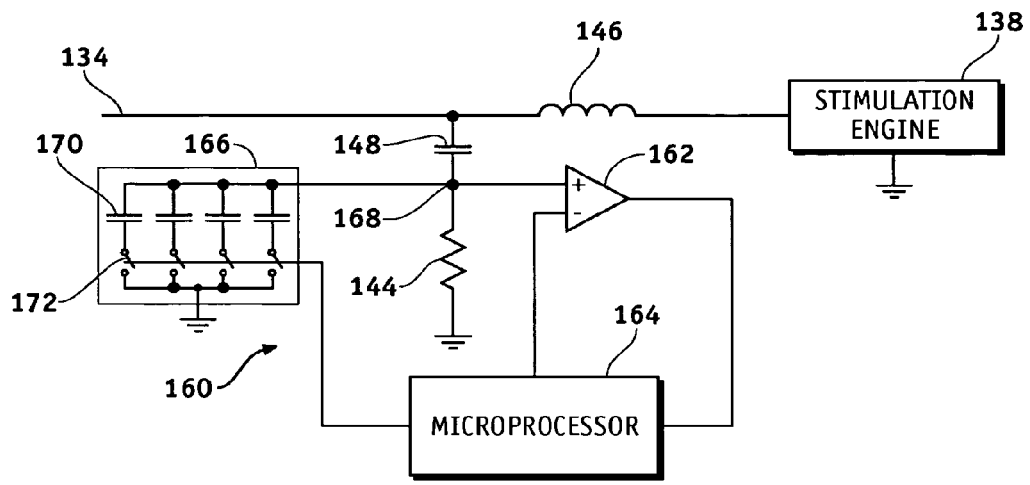
FIG. 21 is a schematic diagram of an impedance monitoring and matching circuit, according to yet a further embodiment of the invention.
Figure 22:
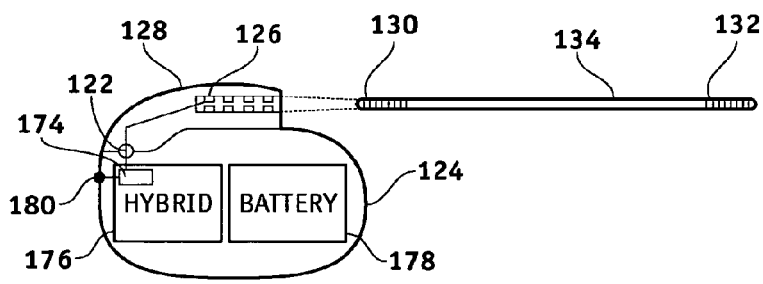
FIGS. 22 and 23 illustrate first and second packaging configurations for the embodiment shown in FIG. 21.
Figure 23:
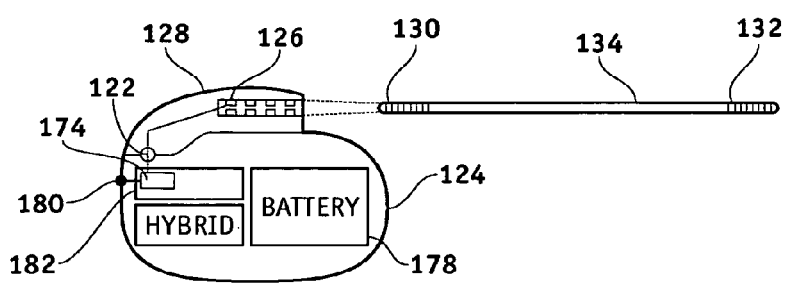

The impedance adjusting circuitry 160 shown in FIG. 21 including, among other components, comparator 162, microprocessor 164, and switched impedance circuit, may be implemented as an integrated circuit 174 that is hermetically sealed within IPG housing 124. It may be included on, for example, the same hybrid assembly 176 that includes other components necessary to produce the desired therapy stimulator including, among other things, sensing, recharge, telemetry, etc. This is illustrated in FIG. 22 which shows battery 178 and hybrid 176 containing circuit 174 hermetically sealed within housing 124. As can be seen, the impedance adjusting circuitry is grounded by coupling it to the metal (e.g. titanium) housing 124 as is shown at 180. Alternatively and more preferably, the impedance adjusting circuitry is implemented on a separate hybrid 182. In still another embodiment, the impedance matching circuit 174 is hermetically housed in a separate encasement (i.e. similar to 142 in FIG. 18).

While at least one exemplary embodiment has been presented in the foregoing detailed description of the invention, it should be appreciated that a vast number of variations exist. For example, while the invention has been described in connection with stimulation systems, the invention is equally applicable to other systems that may be adversely impacted in high frequency environments such as is encountered during an MRI scan. It should also be appreciated that the exemplary embodiment or exemplary embodiments are only examples, and are not intended to limit the scope, applicability, or configuration of the invention in any way. For example, while distal electrodes 114 have been referred to as stimulation electrodes used to deliver therapy to a patient's body tissue; it should be clear to one skilled in the art that electrodes 114 could also be used for sensing.

The foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims.

The invention claimed is:

1. An implantable stimulation system for generating and delivering therapy to a patient, said stimulation system comprising:
   a stimulator for generating the therapy;
   a conductive stimulation lead having a proximal end electrically coupled to said stimulator;
   a stimulation electrode positioned proximate a distal end of said stimulation lead; and
   impedance matching means electrically coupled to said lead for substantially matching the impedance of said stimulator to the characteristic impedance of said lead, the impedance matching means comprising a matching resistor, a variable impedance circuit, and components that monitor a voltage across the matching resistor and vary an impedance of the variable impedance circuit to maintain the voltage across the matching resistor at a maximum.

2. The stimulation system according to claim 1 wherein said stimulator comprises a hermetically sealed encasement and wherein said impedance matching means is housed within said encasement.

3. The stimulation system according to claim 2 wherein said stimulator comprises a first hybrid circuit hermetically sealed in said encasement for generating said therapy and wherein said impedance matching means is configured on said first hybrid circuit.

4. The stimulation system according to claim 2 wherein said stimulator comprises a first hybrid circuit hermetically sealed in said encasement for generating said therapy and wherein said impedance matching means is configured on a second hybrid circuit hermetically sealed within said encasement.

5. The stimulation system according to claim 1 wherein said stimulator comprises a first hermetically sealed encasement and wherein said impedance matching means is hermetically sealed in a second hermetically sealed encasement.

6. An implantable stimulation system for generating and delivering therapy to a patient, said stimulation system comprising:
   a stimulator for generating the therapy;
   a conductive stimulation lead having a proximal end electrically coupled to said stimulator;
   a stimulation electrode positioned proximate a distal end of said stimulation lead; and
   impedance matching circuit electrically coupled to said lead for substantially matching the impedance of said stimulator to the characteristic impedance of said lead, the impedance matching circuit comprising a matching resistor, a variable impedance circuit, and components that monitor a voltage across the matching resistor and vary an impedance of the variable impedance circuit to maintain the voltage across the matching resistor at a maximum.

7. A method for generating and delivering therapy to a patient, said stimulation system comprising:
   providing a stimulator for generating the therapy;
   providing a conductive stimulation lead having a proximal end electrically coupled to said stimulator;
   providing a stimulation electrode positioned proximate a distal end of said stimulation lead; and
   providing an impedance matching circuit electrically coupled to said lead, the impedance matching circuit comprising a matching resistor, a variable impedance circuit, and components;
   monitoring, by the components, a voltage across the matching resistor; and
   varying, by the components, an impedance of the variable impedance circuit to maintain the voltage across the matching resistor at a maximum to substantially match the impedance of said stimulator to the characteristic impedance of said lead.

* * * * *